(12) United States Patent
Lee et al.

(10) Patent No.: US 8,449,929 B2
(45) Date of Patent: May 28, 2013

(54) HERBAL MEDICINAL COMPOSITION AND EXTRACT THEREOF FOR INHIBITING GROWTH OF CANCER CELLS

(76) Inventors: Chen-Yu Lee, Taipei (TW); Jiang Jung Chen, Taichung (TW)

( * ) Notice: Subject to any disclaimer, the term of this patent is extended or adjusted under 35 U.S.C. 154(b) by 0 days.

(21) Appl. No.: 13/613,654

(22) Filed: Sep. 13, 2012

(65) Prior Publication Data

US 2013/0004597 A1    Jan. 3, 2013

Related U.S. Application Data

(62) Division of application No. 12/923,846, filed on Oct. 12, 2010.

(30) Foreign Application Priority Data

Dec. 10, 2009  (TW) ................................ 98142254 A

(51) Int. Cl.
| | |
|---|---|
| *A61K 36/00* | (2006.01) |
| *A61K 36/236* | (2006.01) |
| *A61K 36/539* | (2006.01) |
| *A61K 36/232* | (2006.01) |
| *A61K 36/744* | (2006.01) |
| *A61K 36/804* | (2006.01) |
| *A61K 36/515* | (2006.01) |
| *A61K 36/233* | (2006.01) |
| *A61K 36/284* | (2006.01) |

(52) U.S. Cl.
USPC ............................................ 424/725; 424/757

(58) Field of Classification Search
None
See application file for complete search history.

(56) References Cited

PUBLICATIONS

Bo-Wen Qian,Diagnosis and treatment evaluation of 213 cases of brain tumors,Shanghai Journal of Traditional Chinese Medicine, 1986, p. 6-7, Shanghai University of Traditional Chinese Medicine, China.
Tzu-Ching Kuo,The molecular mechanisms of emodin-induced apoptosis and drug resistance in rat C6 glioma cell line, 2006, China Medical University, Taiwan.
Chin-Ping Lin,Effects of *Scutellaria baicalensis* georgi. on IL-6-Induced dihydrodiol dehydrogenase (DDH) gene expression in non-small cell lung cancer cell line (H23), 2003, National Yang-Ming University, Taiwan.

*Primary Examiner* — Qiuwen Mi
(74) *Attorney, Agent, or Firm* — Bacon & Thomas PLLC

(57) ABSTRACT

The present invention relates to herbal medicinal compositions and extracts thereof for inhibiting growth of cancer cells. One of the examples described in the present invention comprises *Forsythiae fructus*, Menthae Herba, *Gardeniae Fructus*, Scutellariae Radix, Lophatheri Folium, Glycyrrhizae Radix, Rhei Rhizoma, $Na_2SO_4$, and Atractylodis Rhizoma. The residual examples are described herein.

2 Claims, 3 Drawing Sheets

HERBAL MEDICINAL COMPOSITION AND EXTRACT THEREOF FOR INHIBITING GROWTH OF CANCER CELLS

This application is a divisional application of pending U.S. patent application Ser. No. 12/923,846, filed Oct. 12, 2010 (of which the entire disclosure of the pending, prior application is hereby incorporated by reference).

BACKGROUND OF THE INVENTION

1. Field of the Invention

The present invention relates to herbal medicinal compositions and extracts thereof for inhibiting growth of cancer cells and, more particularly, to herbal medicinal compositions and extracts thereof for inhibiting growth of lung cancer cells.

2. Description of Related Art

Cancers have been one of ten leading causes of death in the last continuous 27 years. The main cause of cancer is abnormality of cells which undergo self-division continuously to form more and more abnormal cells, i.e., cancers.

In common tumor cells, some cancer cells have characteristics of stem cells. Although such cancer cells are in a small number, they can undergo cell division and differentiation continuously, similar to stem cells, and thus are so called "cancer stem cells". Since cancer stem cells have extremely high drug resistance, it is difficult for chemotherapeutic agents of modern (Western) medicine to exterminate them. Accordingly, it is often heard that cancer recurrence happens in many patients post-chemotherapy. In addition, standard therapies currently known in biomedical science are still unable to kill such cancer stem cells.

Furthermore, surgical operations, radiotherapies, chemotherapies, hormone therapies, biological therapies, and so on in modern medical science may incur strongly unfavorable side effects to patients. Therefore, it is a significant breakthrough if a cancer can be treated by a therapy which is relatively gentle and able to inhibit development of cancer stem cells.

Currently, people believe that the use of Chinese herbal medicine to treat patients is both a gentle therapy and highly acceptable in commerce. Hence, if a developed herbal medicinal composition is evidenced to inhibit cancer cells or block division of cancer stem cells, it will be considerably helpful to the treatment of cancers.

SUMMARY OF THE INVENTION

The object of the present invention is to provide a herbal medicinal composition and an extract thereof for inhibiting growth of cancer cells such as lung cancer cells.

To achieve the object, one aspect of the present invention provides a herbal medicinal composition for inhibiting cancer cells including: Gentianae Scabrae Radix (*Gentiana scabra* Bunge), Scutellariae Radix (*Scutellaria baicalensis* Georgi), Gardeniae Fructus (*Gardenia jasminoides* Ellis), Anelicae Sinensis Radix (*Angelica sinensis* Diels), Rehmanniae Radix (*Rehmannia glutinosa* Libosch. f. hueichingensis (Chao et Schih) Hsiao), Hocquartiae Caulis (*Hocquartia manshuriensis* (Kom.) Nakai), Bupleuri Radix (*Bupleurum falcatum* Linne), Plantaginis Semen (*Plantago asiatica* Linne), Atractylodis Rhizoma (*Atractylodes lancea* De Candolle), Alismatis Rhizoma (*Alisma plantago—aquatica* L. var. *orientale* SAM.), and Glycyrrhizae Radix (*Glycyrrhiza uralensis* Fischer et DC). This herbal medicinal composition is extracted, i.e., Gentianae Scabrae Radix, Scutellariae Radix, Gardeniae Fructus, Anelicae Sinensis Radix, Rehmanniae Radix, Hocquartiae Caulis, Bupleuri Radix, Plantaginis Semen, Atractylodis Rhizoma, Alismatis Rhizoma, and Glycyrrhizae Radix are mixed, extracted with water under heating, and then filtrated to remove the dreg thereof. A herbal medicinal extract can be obtained and it also can inhibit growth of cancer cells.

Preferably, the Gentianae Scabrae Radix is comprised in an amount of 1.5-6 parts by weight, the Scutellariae Radix is comprised in an amount of 1.5-6 parts by weight, the Gardeniae Fructus is comprised in an amount of 1.5-6 parts by weight, the Anelicae Sinensis Radix is comprised in an amount of 1.5-6 parts by weight, the Rehmanniae Radix is comprised in an amount of 1.5-6 parts by weight, the Hocquartiae Caulis is comprised in an amount of 1.5-6 parts by weight, the Bupleuri Radix is comprised in an amount of 1.5-6 parts by weight, the Plantaginis Semen is comprised in an amount of 1.5-6 parts by weight, the Atractylodis Rhizoma is comprised in an amount of 2-8 parts by weight, the Alismatis Rhizoma is comprised in an amount of 2-8 parts by weight, and the Glycyrrhizae Radix is comprised in an amount of 2.5-10 parts by weight.

More preferably, the Gentianae Scabrae Radix is comprised in an amount of 2-4 parts by weight, the Scutellariae Radix is comprised in an amount of 2-4 parts by weight, the Gardeniae Fructus is comprised in an amount of 2-4 parts by weight, the Anelicae Sinensis Radix is comprised in an amount of 2-4 parts by weight, the Rehmanniae Radix is comprised in an amount of 2-4 parts by weight, the Rehmanniae Radix is comprised in an amount of 2-4 parts by weight, the Bupleuri Radix is comprised in an amount of 2-4 parts by weight, the Plantaginis Semen is comprised in an amount of 2-4 parts by weight, the Atractylodis Rhizoma is comprised in an amount of 3-6 parts by weight, the Alismatis Rhizoma is comprised in an amount of 3-6 parts by weight, and the Glycyrrhizae Radix is comprised in an amount of 4-7 parts by weight.

Another aspect of the present invention provides a herbal medicinal composition for inhibiting cancer cells including: Forsythiae fructus (*Forsythia suspense* (Thunb.) Vahl), Menthae Herba (*Mentha haploclyx* BRIQ.), Gardeniae Fructus, Scutellariae Radix, Lophatheri Folium (*Lophatherurn gracile* Brongniart), Glycyrrhizae Radix, Rhei Rhizoma (*Rheum palmatum* Linne), $Na_2SO_4$, and Atractylodis Rhizoma. This herbal medicinal composition is extracted, i.e., *Forsythiae fructus*, Menthae Herba, Gardeniae Fructus, Scutellariae Radix, Lophatheri Folium, Glycyrrhizae Radix, Rhei Rhizoma, $Na_2SO_4$, and Atractylodis Rhizoma are mixed, extracted with water under heating, and then filtrated to remove the dreg thereof. A herbal medicinal extract can be obtained and it can inhibit growth of cancer cells.

Preferably, the Forsythiae fructus is comprised in an amount of 1.5-6 parts by weight, the Menthae Herba is comprised in an amount of 1.5-6 parts by weight, the Gardeniae Fructus is comprised in an amount of 1.5-6 parts by weight, the Scutellariae Radix is comprised in an amount of 1.5-6 parts by weight, the Lophatheri Folium is comprised in an amount of 1.5-6 parts by weight, the Glycyrrhizae Radix is comprised in an amount of 1.5-6 parts by weight, the Rhei Rhizoma is comprised in an amount of 0.5-2 parts by weight, the $Na_2SO_4$ is comprised in an amount of 0.5-2 parts by weight, and the Atractylodis Rhizoma is comprised in an amount of 2-8 parts by weight.

More preferably, the *Forsythiae fructus* is comprised in an amount of 2-4 parts by weight, the Menthae Herba is comprised in an amount of 2-4 parts by weight, the Gardeniae Fructus is comprised in an amount of 2-4 parts by weight, the Scutellariae Radix is comprised in an amount of 2-4 parts by weight, the Lophatheri Folium is comprised in an amount of 2-4 parts by weight, the Glycyrrhizae Radix is comprised in an amount of 2-4 parts by weight, the Rhei Rhizoma is comprised in an amount of 0.75-1.5 parts by weight, the $Na_2SO_4$ is comprised in an amount of 0.75-1.5 parts by weight, and the Atractylodis Rhizoma is comprised in an amount of 3-6 parts by weight.

Still another aspect of the present invention provides a herbal medicinal composition for inhibiting cancer cells including: Anelicae Sinensis Radix, Ligustici Rhizoma (*Ligusticum chuanxiong* Hortorum), Paeoniae (Ovatae) Radix Rubra (*Paeonia veitchii* Lynch.), Rehmanniae Radix, Glycyrrhizae Radix, Scutellariae Radix, Chinese Wolfberry Root-bark (*Lycium chinense* Mill. Root), Peony Root-bark (*Paeonia suffruticosa* Andr. Root), and Atractylodis Rhizoma. This herbal medicinal composition is extracted, i.e., Anelicae Sinensis Radix, Ligustici Rhizoma, Paeoniae (Ovatae) Radix Rubra, Rehmanniae Radix, Glycyrrhizae Radix, Scutellariae Radix, Chinese Wolfberry Root-bark, Peony Root-bark, and Atractylodis Rhizoma are mixed, extracted with water under heating, and then filtrated to remove the dreg thereof. A herbal medicinal extract can be obtained and it can inhibit growth of cancer cells.

Preferably, the Anelicae Sinensis Radix is comprised in an amount of 1.5-6 parts by weight, the Ligustici Rhizoma is comprised in an amount of 1.5-6 parts by weight, the Paeoniae (Ovatae) Radix Rubra is comprised in an amount of 1.5-6 parts by weight, the Rehmanniae Radix is comprised in an amount of 1.5-6 parts by weight, the Glycyrrhizae Radix is comprised in an amount of 1.5-6 parts by weight, the Scutellariae Radix is comprised in an amount of 1.5-6 parts by weight, the Chinese Wolfberry Root-bark is comprised in an amount of 2,5-10 parts by weight, the Peony Root-bark is comprised in an amount of 2.5-10 parts by weight, and the Atractylodis Rhizoma is comprised in an amount of 2-8 parts by weight.

More preferably, the Anelicae Sinensis Radix is comprised in an amount of 2-4 parts by weight, the Ligustici Rhizoma is comprised in an amount of 2-4 parts by weight, the Paeoniae (Ovatae) Radix Rubra is comprised in an amount of 2-4 parts by weight, the Rehmanniae Radix is comprised in an amount of 2-4 parts by weight, the Glycyrrhizae Radix is comprised in an amount of 2-4 parts by weight, the Scutellariae Radix is comprised in an amount of 2-4 parts by weight, the Chinese Wolfberry Root-bark is comprised in an amount of 4-7 parts by weight, the Peony Root-bark is comprised in an amount of 4-7 parts by weight, and the Atractylodis Rhizoma is comprised in an amount of 2-8 parts by weight.

Yet a further aspect of the present invention provides a herbal medicinal composition for inhibiting cancer cells including: Anelicae Sinensis Radix, Ligustici Rhizoma, Peony Root (*Paeonia lactiflora* Pall.), Rehmanniae Radix, Atractylodis Rhizoma (*Atractylodes ovata* De Canndolle), Glycyrrhizae Radix, Dipsaci Radix (*Dipsacus asper* Wall.), Eucommia Bark (*Eucommia ulmoides* Oliv), Scutellariae Radix, Dioscoreae Rhizoma (*Dioscorea opposita* Thunb.), and Asiatic Wormwood (*Artemisia argyi* Levi. et Vant.). This herbal medicinal composition is extracted, i.e., Anelicae Sinensis Radix, Ligustici Rhizoma, Peony Root, Rehmanniae Radix, Atractylodis Rhizoma, Glycynthizae Radix, Dipsaci Radix, Eucommia Bark, Scutellariae Radix, Dioscoreae Rhizoma, and Asiatic Wormwood. are mixed, extracted with water under heating, and then filtrated to remove the dreg thereof. A herbal medicinal extract can be obtained and it can inhibit growth of cancer cells.

Preferably, the Anelicae Sinensis Radix is comprised in an amount of 1.5-6 parts by weight, the Ligustici Rhizoma is comprised in an amount of 1.5-6 parts by weight, the Peony Root is comprised in an amount of 1.5-6 parts by weight, the Rehmanniae Radix is comprised in an amount of 1.5-6 parts by weight, the Atractylodis Rhizoma is comprised in an amount of 1.5-6 parts by weight, the Glycyrrhizae Radix is comprised in an amount of 1.5-6 parts by weight, the Dipsaci Radix is comprised in an amount of 1.5-6 parts by weight, the Eucommia Bark is comprised in an amount of 1.5-6 parts by weight, the Scutellariae Radix is comprised in an amount of 1.5-6 parts by weight, the Dioscoreae Rhizoma is comprised in an amount of 2.5-10 parts by weight, and the Asiatic Wormwood. is comprised in an amount of 2.5-10 parts by weight.

More preferably, the Anelicae Sinensis Radix is comprised in an amount of 2-4 parts by weight, the Ligustici Rhizoma is comprised in an amount of 2-4 parts by weight, the Peony Root is comprised in an amount of 2-4 parts by weight, the Rehmanniae Radix is comprised in an amount of 2-4 parts by weight, the Atractylodis Rhizoma is comprised in an amount of 2-4 parts by weight, the Glycyrrhizae Radix is comprised in an amount of 2-4 parts by weight, the Dipsaci Radix is comprised in an amount of 2-4 parts by weight, the Eucommia Bark is comprised in an amount of 2-4 parts by weight, the Scutellariae Radix is comprised in an amount of 2-4 parts by weight, the Dioscoreae Rhizoma is comprised in an amount of 4-7 parts by weight, and the Asiatic Wormwood. is comprised in an amount of 4-7 parts by weight.

Still another aspect of the present invention provides a herbal medicinal composition for inhibiting cancer cells including: Cinnamomum Ramulus (*Cinnamomum cassia* Presl.), Paeoniae (Ovatae) Radix Rubra, Glycyrrhizae Radix, Zingiberis Rhizoma (*Zingiber officinale* Roscoe), Scutellariae Radix, and Jujubae Fructus (*Ziziphus jujuba* Mill.). This herbal medicinal composition is extracted, i.e., Cinnamomum Ramulus, Paeoniae (Ovatae) Radix Rubra, Glycyrrhizae Radix, Zingiberis Rhizoma, Scutellariae Radix, and Jujubae Fructus. are mixed, extracted with water under heating, and then filtrated to remove the dreg thereof. A herbal medicinal extract can be obtained and it can inhibit growth of cancer cells.

Preferably, the Cinnamomum Ramulus is comprised in an amount of 2.5-10 parts by weight, the Paeoniae (Ovatae) Radix Rubra is comprised in an amount of 2.5-10 parts by weight, the Glycyrrhizae Radix is comprised in an amount of 2.5-10 parts by weight, the Zingiberis Rhizoma is comprised in an amount of 2.5-10 parts by weight, the Scutellariae Radix is comprised in an amount of 1.5-6 parts by weight, and the Jujubae Fructus. is comprised in an amount of 2.5-10 parts by weight.

More preferably, the Cinnamomum Ramulus is comprised in an amount of 4-7 parts by weight, the Paeoniae (Ovatae) Radix Rubra is comprised in an amount of 4-7 parts by weight, the Glycyrrhizae Radix is comprised in an amount of 4-7 parts by weight, the Zingiberis Rhizoma is comprised in an amount of 4-7 parts by weight, the Scutellariae Radix is comprised in an amount of 2-4 parts by weight, and the Jujubae Fructus. is comprised in an amount of 4-7 parts by weight.

Still a further aspect of the present invention provides a herbal medicinal composition for inhibiting cancer cells including: Cimicifugae Rhizoma (*Cimicifuga herackifolia* Kam), Rehmanniae Radix, Paeoniae (Ovatae) Radix Rubra, Peony Root-bark, and Scutellariae Radix. This herbal medicinal composition is extracted, i.e., Cimicifugae Rhizoma, Rehmanniae Radix, Paeoniae (Ovatae) Radix Rubra, Peony Root-bark, and Scutellariae Radix are mixed, extracted with water under heating, and then filtrated to remove the dreg thereof. A herbal medicinal extract can be obtained and it can inhibit growth of cancer cells.

Preferably, the Cimicifugae Rhizoma is comprised in an amount of 1-4 parts by weight, the Rehmanniae Radix is comprised in an amount of 7.5-30 parts by weight, the Paeoniae (Ovatae) Radix Rubra is comprised in an amount of 5-20 parts by weight, the Peony Root-bark is comprised in an amount of 5-20 parts by weight, and the Scutellariae Radix is comprised in an amount of 5-20 parts by weight.

More preferably, the Cimicifugae Rhizoma is comprised in an amount of 1.5-3 parts by weight, the Rehmanniae Radix is comprised in an amount of 10-20 parts by weight, the Paeoniae (Ovatae) Radix Rubra is comprised in an amount of 8-15 parts by weight, the Peony Root-bark is comprised in an amount of 8-15 parts by weight, and the Scutellariae Radix is comprised in an amount of 8-15 parts by weight.

Besides, in the above mentioned herbal medicinal composition and the herbal medicinal extract thereof, the temperature and time of the heating, the amount of used water, and condensing ratio of the extract are not specifically limited. Preferably, the heating is to heat the water to 90-100° C. for 60-90 mins, the water is used in an amount of 5-15 times the total weight of the mixture, and the extract is condensed to ½-¼ weight of the water by heating.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
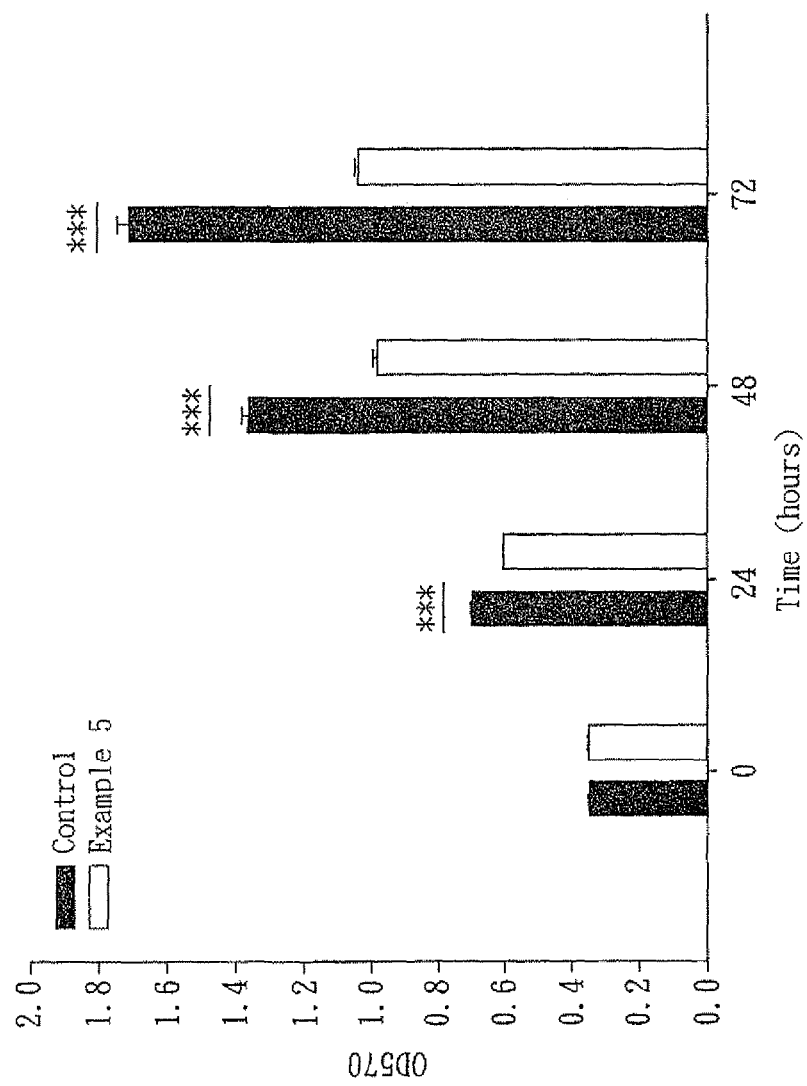
FIG. 1 is a diagram showing the relation between the survival rate of A549 lung cancer cells and the time of treating A549 lung cancer cells with the extract of Example 5 of the present invention, in which *** represents p<0.001 after Student's t test.

According to the specific embodiments illustrating the practice of the present invention, a person having ordinary skill in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

EXAMPLE 1

Gentianae Scabrae Radix (11.25 g), Scutellariae Radix (11.25 g), Gardeniae Fructus (11.25 g), Anelicae Sinensis Radix (11.25 g), Rehmanniae Radix (11.25 g), Rehmanniae Radix (11.25 g), Bupleuri Radix (11.25 g), Plantaginis Semen (11.25 g), Atractylodis Rhizoma (15 g), Alismatis Rhizoma (15 g), and Glycyrrhizae Radix (18.75 g) all were cut into slices, respectively. A mixture containing the abovementioned herbal medicinal materials was extracted with water (1200 g) under heating to 90° C. or more for 60-90 minutes, condensed into 400 g, and then filtrated to remove the dreg thereof to afford an extract.

EXAMPLE 2

*Forsythiae fructus* (11.25 g), Menthae Herba (11.25 g), Gardeniae Fructus (11.25 g), Scutellariae Radix (11.25 g), Lophatheri Folium (11.25 g), Glycyrrhizae Radix (11.25 g), Rhei Rhizoma (3.75 g), $Na_2SO_4$ (3.75 g), and Atractylodis Rhizoma (15 g) all were cut into slices, respectively. A mixture containing the abovementioned herbal medicinal materials was extracted with water (1200 g) under heating to 90° C. or more for 60-90 minutes, condensed into 400 g, and then filtrated to remove the dreg thereof to afford an extract.

EXAMPLE 3

Anelicae Sinensis Radix (11.25 g), Ligustici Rhizoma (11.25 g), Paeoniae (Ovatae) Radix Rubra (11.25 g), Rehmanniae Radix (11.25 g), Glycyrrhizae Radix (11.25 g), Scutellariae Radix (11.25 g), Chinese Wolfberry Root-bark (18.75 g), Peony Root-bark (18.75 g), and Atractylodis Rhizoma (15 g) all were cut into slices, respectively. A mixture containing the abovementioned herbal medicinal materials was extracted with water (1200 g) under heating to 90° C. or more for 60-90 minutes, condensed into 400 g, and then filtrated to remove the dreg thereof to afford an extract.

EXAMPLE 4

Anelicae Sinensis Radix (11.25 g), Ligustici Rhizoma (11.25 g), Peony Root (11.25 g), Rehmanniae Radix (11.25 g), Atractylodis Rhizoma (11.25 g), Glycyrrhizae Radix (11.25 g), Dipsaci Radix (11.25 g), Eucommia Bark (11.25 g), Scutellariae Radix (11.25 g), Dioscoreae Rhizoma (18.75 g), and Asiatic Wormwood. (18.75 g) all were cut into slices, respectively. A mixture containing the abovementioned herbal medicinal materials was extracted with water (1200 g) under heating to 90° C. or more for 60-90 minutes, condensed into 400 g, and then filtrated to remove the dreg thereof to afford an extract.

EXAMPLE 5

Cinnamomum Ramulus (18.75 g), Paeoniae (Ovatae) Radix Rubra (18.75 g), Glycyrrhizae Radix (18.75 g), Zingiberis Rhizoma (18.75 g), Scutellariae Radix (11.25 g), and Jujubae Fructus. (18.75 g) all were cut into slices, respectively. A mixture containing the abovementioned herbal medicinal materials was extracted with water (1200 g) under heating to 90° C. or more for 60-90 minutes, condensed into 400 g, and then filtrated to remove the dreg thereof to afford an extract.

EXAMPLE 6

Cimicifugae Rhizoma (7.5 g), Rehmanniae Radix (56.25 g), Paeoniae (Ovatae) Radix Rubra (37.5 g), Peony Root-bark (37.5 g), and Scutellariae Radix (37.5 g) all were cut into slices, respectively. A mixture containing the abovementioned herbal medicinal materials was extracted with water (1200 g) under heating to 90° C. or more for 60-90 minutes, condensed into 400 g, and then filtrated to remove the dreg thereof to afford an extract.

TEST EXAMPLE

Researches have directed that cancer stem cells are those exhibiting characteristics of stem cells in cancer cells. Therefore, if treatment focuses on common cancer cells, cancer stem cells may still survive in a treated tumor. Owing to characteristics of stem cells, the cancer stem cells which survive still can differentiate into commons cancer cells and even form a malignant tumor, resulting in cancer recurrence after treatment. However, if treatment can focus on cancer stem cells, tumors have no survivor of cancer stem cells which can differentiate to supply the number of common cancer cells, and thus can be inhibited.

According to the reported researches, some researchers have isolated cancer stem cells having characteristics of stem cells from A549 lung cancer cells. Therefore, in the following Test Examples of the present invention, the extracts from the herbal medicinal composition of the present invention were analyzed for the survival rate of A549 lung cancer cells. In addition, the cell cycle of cancer cells was checked by flow cytometry to determine whether it was blocked by the extracts of the present invention. The influence of the extracts of the present invention on promotion of cell apoptosis was also confirmed by staining methods. Besides, flow cytometry and two-color fluorescence staining were performed to determine the cytotoxicity of the extracts of the present invention in cancer cells.

TEST EXAMPLE 1

Test for Survival Rate of Cells

A549 lung cancer cells were treated with the extracts of Examples 1-6 respectively with a concentration of 10%, 20%, and 100% for 72 hours, and then their survival rates were determined by an MTT assay. The results are shown in the following Table 1.

TABLE 1

| | Survival Rate Extract | | |
|---|---|---|---|
| | 5 µl | 10 µl | 50 µl |
| | Pure Water | | |
| | 45 µl | 40 µl | 0 µl |
| Example 1 | 96% | 96% | 35% |
| Example 2 | 89% | 83% | 29% |
| Example 3 | 24% | 11% | 5% |
| Example 4 | 107% | 80% | 7% |
| Example 5 | 97% | 77% | 41% |
| Example 6 | 76% | 70% | 12% |

Survival rate (%) = average absorbance of experimental groups/average absorbance of control group
Control group: treated with pure water but without the extracts As listed in Table 1, the survival rates of A549 cancer cells treated after 72 hours reduce as the concentration of the extracts increase.

TEST EXAMPLE 2

Influence of Treating Time on the Survival Rate of the Cancer Cells

According to the result of Test Example 1, it can be seen that a half maximal inhibitory dose of the extract of Example 5 is 35 µl. Therefore, A549 lung cancer cells were treated with the half maximal inhibitory dose (35 µl) for 24, 48, and 72 hours, and were analyzed by an MTT assay to check the survivors thereof. The results are shown in the FIG. 1.

As shown in FIG. 1, compared with the control group of A549 lung cancer cells untreated with the extract of Example 5, the experimental groups thereof treated with the extract of Example 5 for 24, 48, and 72 hours all have reduced survival rates. Furthermore, as the treating time extends, the survival rates have more significant diversity.

TEST EXAMPLE 3

Test of Checking Cell Cycle Block (1) PI staining

Figure 2:
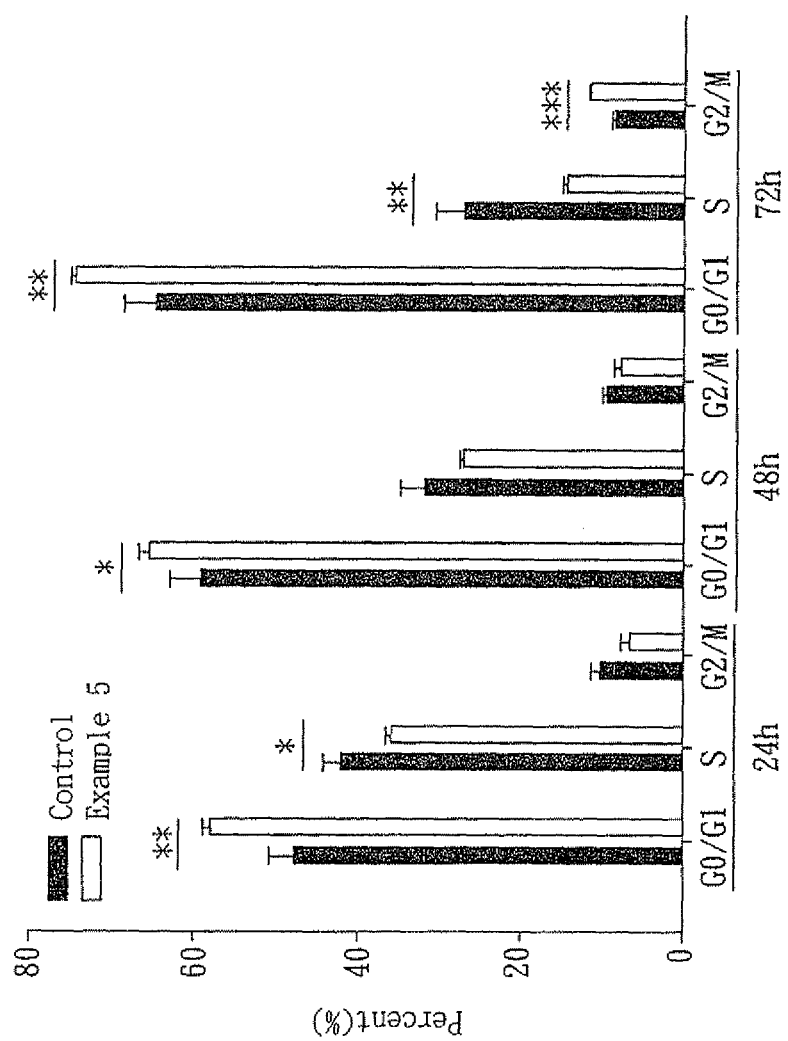
FIG. 2 is a diagram showing the rates of A549 lung cancer cells in G0/G1, S, and G2/M phases posterior to being treated with the extract of Example 5 of the present invention, in which *, , and * represents p<0.05, 0.01, and 0.001 after Student's t test, respectively.

A549 lung cancer cells were treated with the half maximal inhibitory dose (35 µl) of the extract of Example 5 for 24, 48, and 72 hours, and then underwent PI staining followed with flow cytometry to determine DNA level of the lung cancer cells. After analysis of statistics, the result is shown in FIG. 2. In FIG. 2, G0/G1, S, G2/M on the horizontal axis represent specific phases in a cell cycle, and the vertical axis represents cell rates of the distinct phases.

In the present test, the cell rates of A549 lung cancer cells in distinct phase of a cell cycle were observed. The results are shown in FIG. 2. Compared with the control group of A549 lung cancer cells untreated with the extract of Example 5, the experimental groups thereof treated with the extract of Example 5 for 24, 48, and 72 hours all have considerably increased cell rates in the G0/G1 phase. This demonstrates that the extract of Example 5 blocks the cell cycle of A549 lung cancer cells in the G0/G1 phase.

(2) Pi and Ki67 Antibody Co-Staining

A549 lung cancer cells were treated with the half maximal inhibitory dose (35 µl) of the extract of Example 5 for 72 hours, and then underwent PI and Ki67 antibody co-staining followed with flow cytometry to determine the cell rate of the A549 lung cancer cells in the G0 phase. After statistics, the result is shown in FIG. 3.

Figure 3:
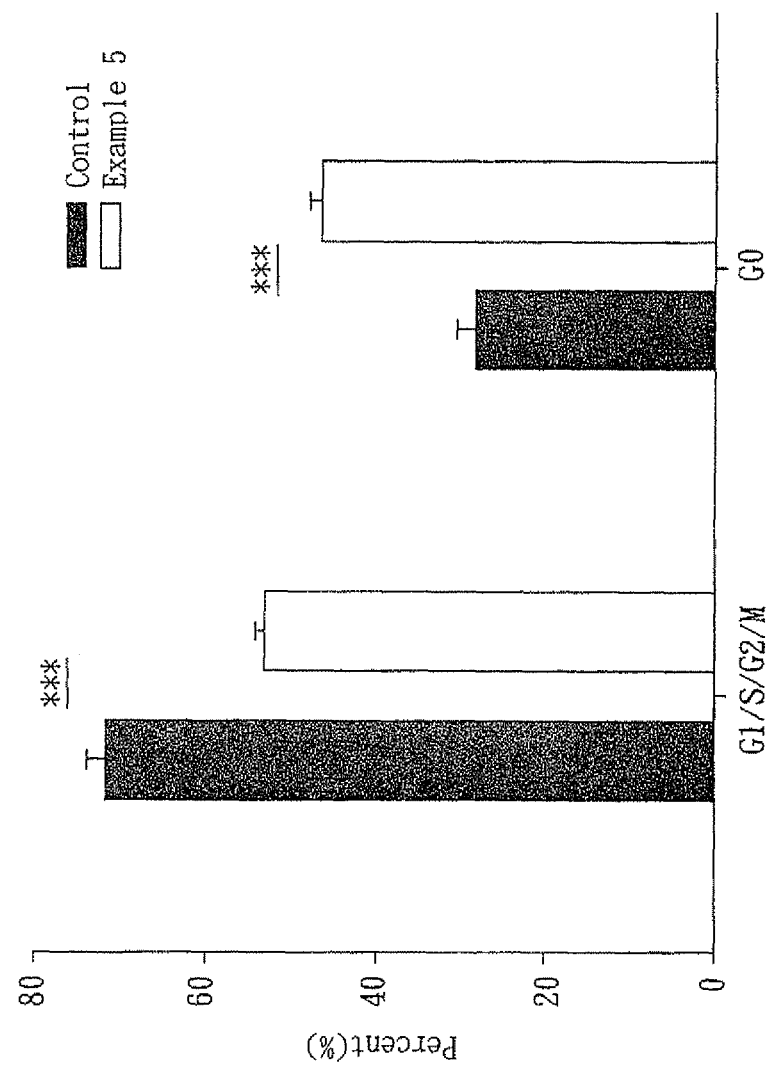
FIG. 3 is a diagram showing the rate of A549 lung cancer cells in G0 phase posterior to being treated with the extract of Example 5 of the present invention, in which *** represents p<0.001 after Student's t test.

As shown in FIG. 3, compared with the control group of A549 lung cancer cells untreated with the extract of Example 5, the experimental group thereof treated with the extract of Example 5 has considerably increased cell rates in the G0 phase. This demonstrates that relatively more A549 lung cancer cells do not accord with a cell cycle and they stay in the G0 phase (not division).

According to the results of the abovementioned test examples, it can be understood that the herbal medicinal composition and extract thereof provided in the present invention can inhibit growth of cancer cells and make the cancer cells stay in the G0 phase so as to block the continuous division of the cancer cells.

Although the present invention has been explained in relation to its preferred embodiment, it is to be understood that many other possible modifications and variations can be made without departing from the scope of the invention as hereinafter claimed.

What is claimed is:

1. An herbal medicinal composition for inhibiting cancer cells, comprising *Gentianae Scabrae* Radix is comprised in an amount of 1.5-6 parts by weight, Scutellariae Radix in an amount of 1.5-6 parts by weight, *Gardeniae Fructus* in an amount of 1.5-6 parts by weight, *Angelicae Sinensis* Radix in an amount of 1.5-6 parts by weight, Rehmanniae Radix in an amount of 1.5-6 parts by weight, Caulis Hocquartiae in an amount of 1.5-6 parts by weight, *Bupleuri* Radix in an amount of 1.5-6 parts by weight, *Plantaginis Semen* in an amount of 1.5-6 parts by weight, *Atractylodis Rhizoma* in an amount of 2-8 parts by weight, *Alismatis Rhizoma* in an amount of 2-8 parts by weight, and Glycyrrhizae Radix in an amount of 2.5-10 parts by weight.

2. A method for making an herbal medicinal extract for inhibiting cancer cells, comprising:
   mixing *Gentianae Scabrae* Radix, Scutellariae Radix, *Gardeniae Fructus, Angelicae Sinensis* Radix, Rehmanniae Radix, Caulis Hocquartiae, *Bupleuri* Radix, *Plantaginis Semen, Atractylodis Rhizoma, Alismatis Rhizoma*, and Glycyrrhizae Radix to form a mixture;
   extracting the mixture with water under heating to form an extract; and
   filtrating the extract to remove dregs of the extract to form the herbal medicinal extract, wherein the herbal medicinal extract comprises the *Gentianae Scabrae* Radix in an amount of 1.5-6 parts by weight, the Scutellariae Radix in an amount of 1.5-6 parts by weight, the *Gardeniae Fructus* in an amount of 1.5-6 parts by weight, the *Angelicae Sinensis* Radix in an amount of 1.5-6 parts by weight, the Rehmanniae Radix in an amount of 1.5-6 parts by weight, the Caulis Hocquartiae in an amount of 1.5-6 parts by weight, the *Bupleuri* Radix in an amount of 1.5-6 parts by weight, the Plantaginis Semen in an amount of 1.5-6 parts by weight, the *Atractylodis Rhizoma* in an amount of 2-8 parts by weight, the *Alismatis Rhizoma* in an amount of 2-8 parts by weight, and the Glycyrrhizae Radix in an amount of 2.5-10 parts by weight.

\* \* \* \* \*